(12) United States Patent
Borodyanski et al.

(10) Patent No.: US 6,524,486 B2
(45) Date of Patent: Feb. 25, 2003

(54) MICROALGAE SEPARATOR APPARATUS AND METHOD

(75) Inventors: Genady Borodyanski, Nesher (IL); Irina Konstantinov, Nesher (IL)

(73) Assignee: Sepal Technologies Ltd., Ofakim (IL)

( * ) Notice: Subject to any disclaimer, the term of this patent is extended or adjusted under 35 U.S.C. 154(b) by 159 days.

(21) Appl. No.: 09/748,249

(22) Filed: Dec. 27, 2000

(65) Prior Publication Data

US 2002/0079270 A1 Jun. 27, 2002

(51) Int. Cl.⁷ .............. A01G 7/00; B01D 1/02; C02F 1/24
(52) U.S. Cl. ............ 210/703; 210/744; 210/768; 210/769; 210/770; 210/602; 210/202; 210/205; 210/221.2; 210/295; 47/1.4
(58) Field of Search .................. 210/703, 744, 210/770, 769, 768, 602, 205, 206, 221.2, 202, 295, 109; 47/1.4

(56) References Cited

U.S. PATENT DOCUMENTS 4,834,872 A  *  5/1989  Overath
5,951,875 A  *  9/1999  Kanel et al.

OTHER PUBLICATIONS

Shelef et al; "Algae Mass Production as an integral part of a wastewater treatment and Reclamation System"; Algae Biomass edited by Shelef And Soeder; 1980; Elsevier/North–Holland Biomedical Press pp. 163–189.*

* cited by examiner

Primary Examiner—Thomas M. Lithgow
(74) Attorney, Agent, or Firm—Edward Langer, Pat. Atty.; Shiboleth, Yisraeli, Rober Zisman & Co

(57) ABSTRACT

An apparatus and method for separating microalgae from water without rupturing cells. The method comprises the steps of flocculation, flotation and dehydration. Microalgae suspension from a reservoir is passed to a mixer unit where flocculation is carried out, using modified starch or other flocculating agents. The suspension is then directed to a flotation column. Dissolved gas in water is transferred to the flotation column through a disperser. A layer of foam containing microalgae is formed on the liquid layer in the column, which can be skimmed off through an overflow outlet. The flotation column is a telescopic column of adjustable height, which enables the position of the overflow outlet to be aligned with the level of the foam layer for efficient foam removal. Foam containing microalgae is then passed to a filtration unit for cloth filtration, followed by drying in a drying chamber.

18 Claims, 3 Drawing Sheets

MICROALGAE SEPARATOR APPARATUS AND METHOD

FIELD OF THE INVENTION

The invention relates to an apparatus and method for separation of microalgae from water without rupturing cells, in order to obtain dry, concentrated biomass and in particular to a system including a flotation column provided with an overflow outlet of adjustable height.

BACKGROUND OF THE INVENTION

Microalgae are unicellular organisms, which produce oxygen by photosynthesis. Over 100,000 species of microalgae are known and discovering new uses for them is a major component in the development of industries based on biotechnology. Microalgae are particularly useful because of their high growth rate and tolerance to varying environmental conditions.

Microalgae have uses in the production of vitamins, pharmaceuticals, natural dyes, as a source of fatty acids, proteins and other biochemicals in health food products. Factors derived from microalgae have also been claimed to prevent neuro-degenerative diseases such as Alzheimer's and macular degeneration, which leads to blindness. They are effective in the biological control of agricultural pests; as soil conditioners and biofertilizers in agriculture; for the production of oxygen and removal of nitrogen, phosphorus and toxic substances in sewage treatment; and in biodegradation of plastics.

Microalgae have use as a renewable biomass source for the production of a diesel fuel substitute (biodiesel) and for electricity generation. Burning of fossil fuels in power plants is a primary contributor to excess carbon dioxide in the atmosphere, which has been linked to global climatic change. Release of carbon dioxide into the atmosphere can be significantly reduced by operation of microalgae fuel farms in tandem with fossil fuel plants to scrub CO2 from flue gases. If the microalgae are used to produce fuel, a mass culture facility reduces the CO2 emission from the power plant by approximately 50%.

Due to the wide range of uses of microalgae and microalgae-based products, an effective method of harvesting microalgae is essential. The effective separation of microalgae from water is a crucial step in this process.

Conventional methods for harvesting microalgae are centrifugation, sedimentation, filtration under pressure through a microstrainer and flocculation with chemical flocculants. The disadvantages of these methods are as follows:

1. Centrifugation

This method is long, complicated and costly. It causes cells to rupture, thereby causing many of the biologically and chemically active materials to be lost or damaged. The cost of electricity, reagents and maintenance of centrifuge may constitute up to 25% of the total production cost. The process is complex, a large capital investment is required, and a relatively low yield is obtained. Operation of the machine is also extremely noisy. In addition, centrifugation is unsuitable for separation of very small microalgae, since for organisms of less than 5 mk a very high rotational speed is necessary (>10,000 rev/min).

2. Sedimentation

This method gives inefficient concentration of biomass.

3. Filtration Under Pressure through a Microstrainer

This method has the advantage of low power requirement (0.2–0.4 kW). However, it is suitable only for fairly large microalgae (e.g. Spirulina Platensis, 300 micrometers long or Coelastrium Proboseidum 30 micrometers diameter).

4. Flocculation

This method uses chemical flocculants, e.g. aluminium sulfate. This limits applicability for food and pharmaceutical products, as it requires subsequent removal, thereby increasing production costs. Dehydration is then usually carried out either by artificial heat or sun drying. The former is costly. It involves ejecting the algae suspension containing 6–8% dry matter onto a rotating steam heated drum which heats the cells to 120 degrees in a few seconds. A 1 kg dry algae mass requires evaporation of 18 kg water. The sun drying method is very slow.

Guelcher et al (U.S. Pat. No. 5,910,254) and Kanel et al., (U.S. Pat. No. 5,951,875) describe an adsorptive bubble separation method for dewatering suspensions of microalgae. This invention involves an apparatus having a number of complex recirculation zones to eliminate liquid communication while generating a froth consisting of bubbles and adsorbed algal cells that can be separated from the aqueous suspension.

A column flotation method and apparatus for the removal of mineral ores from a liquid suspension has been described by Jameson (U.S. Pat. No. 4,938,865). In this method, the liquid is introduced into the upper part of a first column into which air is entrained forming a downwardly moving foam bed. Liquid and entrained air from the lower part of the first column is passed into a second column and froth from the foam is allowed to separate from liquid in the second column forming a liquid-froth interface. The froth layer containing the floatable particles rises upwards to discharge through a suitably placed outlet.

In this apparatus, the liquid-froth interface must therefore be adjusted to the fixed level of the outlet. Precise adjustment of the foam level is difficult to implement, resulting in a certain proportion of particles, contained in the froth layer, to remain below the outlet level and therefore to remain in the column, thus reducing the yield.

A further feature of this invention is that liquid is injected in the form of a jet which points downwards and entrains the air, creating a bed of dense foam. This method, if applied to algae would cause a significant amount of cell breakage. In addition, frothing agents are generally added to the solution to create a stable foam layer, which is undesirable in the case of algae intended for use in health or food products.

Therefore, it would be desirable to provide a method for separation of microalgae from water which is less costly, easier to use, involves a lower energy consumption, provides a high yield and preserves the integrity of the cell structure, enabling retention of desirable cell components.

SUMMARY OF THE INVENTION

Accordingly, it is the object of the present invention to provide an efficient and cost-effective method of obtaining dry, concentrated biomass from an aqueous solution of microalgae, without causing the cells to be ruptured.

The present invention describes a three-stage process, comprising flocculation, flotation and dehydration. The invention is suitable for enterprises engaged in growing microalgae of all types and therefore for all applications, including food and pharmaceutical products. It can be adapted towards specific species if necessary. The system is cheaper and faster than currently available methods and retains many of the properties of the microalgae which are lost in conventional technologies. The system is simple to use and inexpensive to maintain. The separator has no internal moving parts. No special operator training is required in order to operate and maintain the system.

In a preferred embodiment of the invention, microalgae suspension from a reservoir is passed to a mixer unit where flocculation occurs. The flocculated suspension is then directed to a flotation column of adjustable height into which $CO_2$ (or air) is fed through a disperser, producing bubbles of uniform size. The bubbles carry electrostatically adsorbed flocs to the surface of the liquid, forming a foam layer, which is skimmed off at the top through an overflow outlet. Purified water is discharged through the bottom. Microalgae are filtered through cloth, dried and packed. Solid biomass is passed through a filtration unit and further dried in a drying chamber.

A feature of the invention is the telescopic design of the column, which allows the height to be adjusted so that the position of the overflow outlet corresponds to the position of the foam layer, resulting in efficient removal of foam.

The advantages of the present invention include high yield, absence of rotating parts; a low power requirement (power is needed only for driving the air blower); the possibility of controlling air flow rate and dispersion; small floor space requirement; low capital investment and suitable for use with most species of microalgae, including those as small as 0.5 um. The present invention also preserves the intact structure of the cells and is almost noiseless.

Other features and advantages of the method will become apparent from the following drawings and description.

BRIEF DESCRIPTION OF DRAWINGS

For a better understanding of the invention, reference is made to the accompanying drawings, in which like numbers designate corresponding elements or sections throughout, and in which.

DETAILED DESCRIPTION OF THE INVENTION

A process comprising the stages of flocculation, flotation and dehydration is described in the present invention. To better understand the invention, each of the three stages is generally defined as follows:

1. Flocculation

Flocculation is the process by which microalgae of microscopic size, suspended in a liquid medium, form stable aggregates.

2. Flotation

Bubbles possess a static charge so organic material in liquid medium becomes attached to oppositely charged bubbles. Bubbles rise to the surface of the liquid medium carrying electrostatically adsorbed flocs with them, forming a foam layer. The froth containing the algae is skimmed off through an overflow outlet.

3. Dehydration

Foam with algae is separated from froth. Microalgae are filtered through cloth, dried and packed. Removal of solid biomass from aqueous suspension is carried out periodically by filtration. After filtration, the biomass is further dehydrated in a drying chamber.

Figure 1:
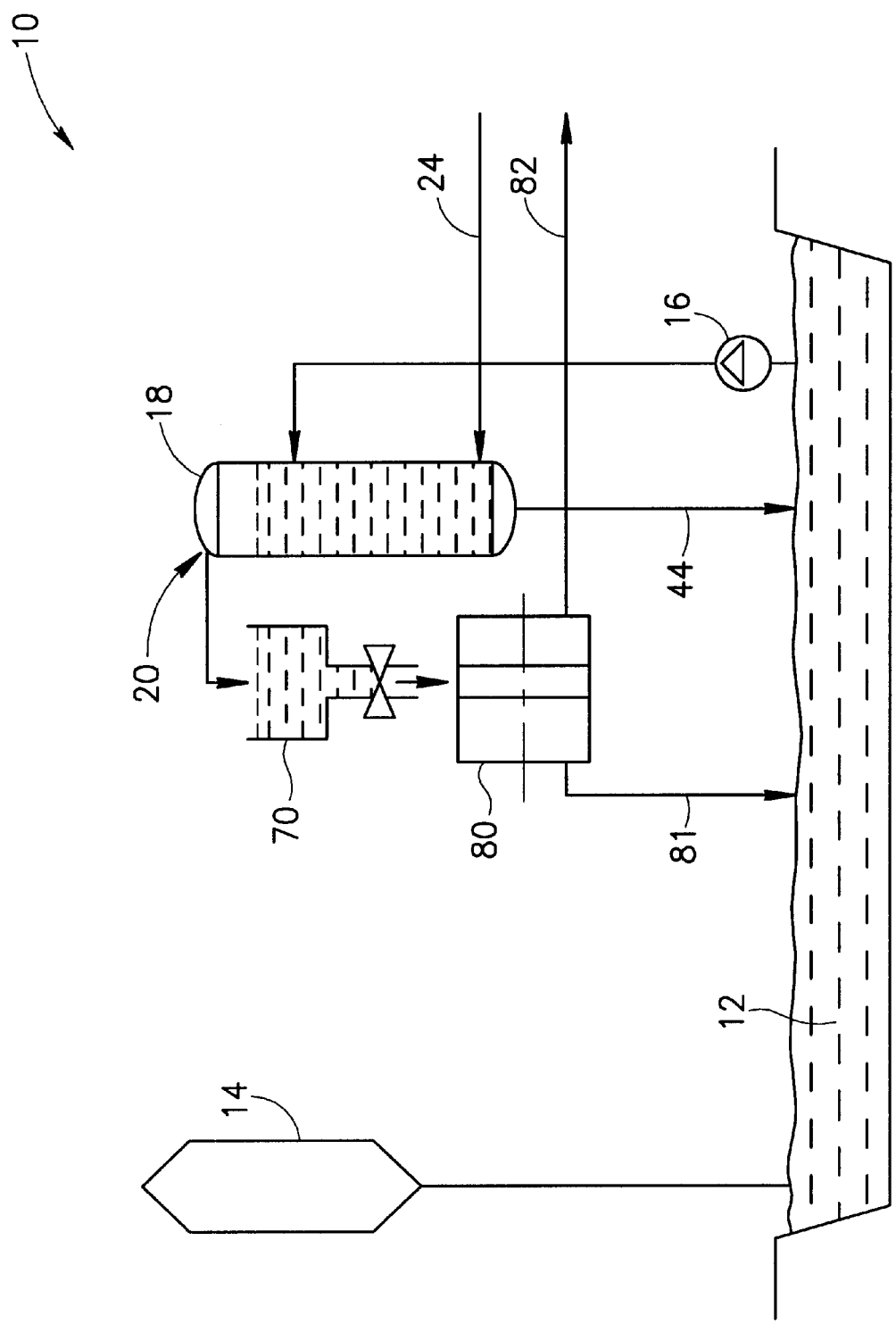
FIG. 1 schematically illustrates the process by which dry microalgae are obtained from a solution of algae in mass culture.

Referring now to FIG. 1, there is seen a microalgae production system 10, typically comprising a pond 12, a source of CO2 14, a pump 16, a microalgae separator 18, a foam overflow outlet 20, a filtration unit 70 and a drying chamber 80. This system operates according to the processes of flocculation, flotation and dehydration. The above-mentioned processes are further expanded upon in the context of the present invention.

In system 10, microalgae are grown in an open-air raceway type shallow pond 12 i.e. one in which mixing is carried out by operation of paddle wheels, connected with a source 14 of CO2. Pond 12 is filled with fresh or sea-water. The open air surface of pond 12 permits absorption of sunlight. The CO2 is fixed in system 10 by the microalgae and converted into organic matter by solar energy.

Microalgae suspension from pond 12 is transferred by operation of pump 16 to microalgae separator 18, in which the processes of flocculation and flotation are carried out. Dissolved air or CO2 in water is fed into microalgae separator 18 through a disperser 24. Foam containing microalgae obtained in the flotation process is skimmed off via an overflow outlet 20. Purified water passes out of microalgae separator 18 via outlet 44. The foam is passed to a filtration unit 70 and is further dried in a drying chamber 80, resulting in dry biomass 82. Purified water passes out of chamber 80 through outlet 81.

Figure 2:
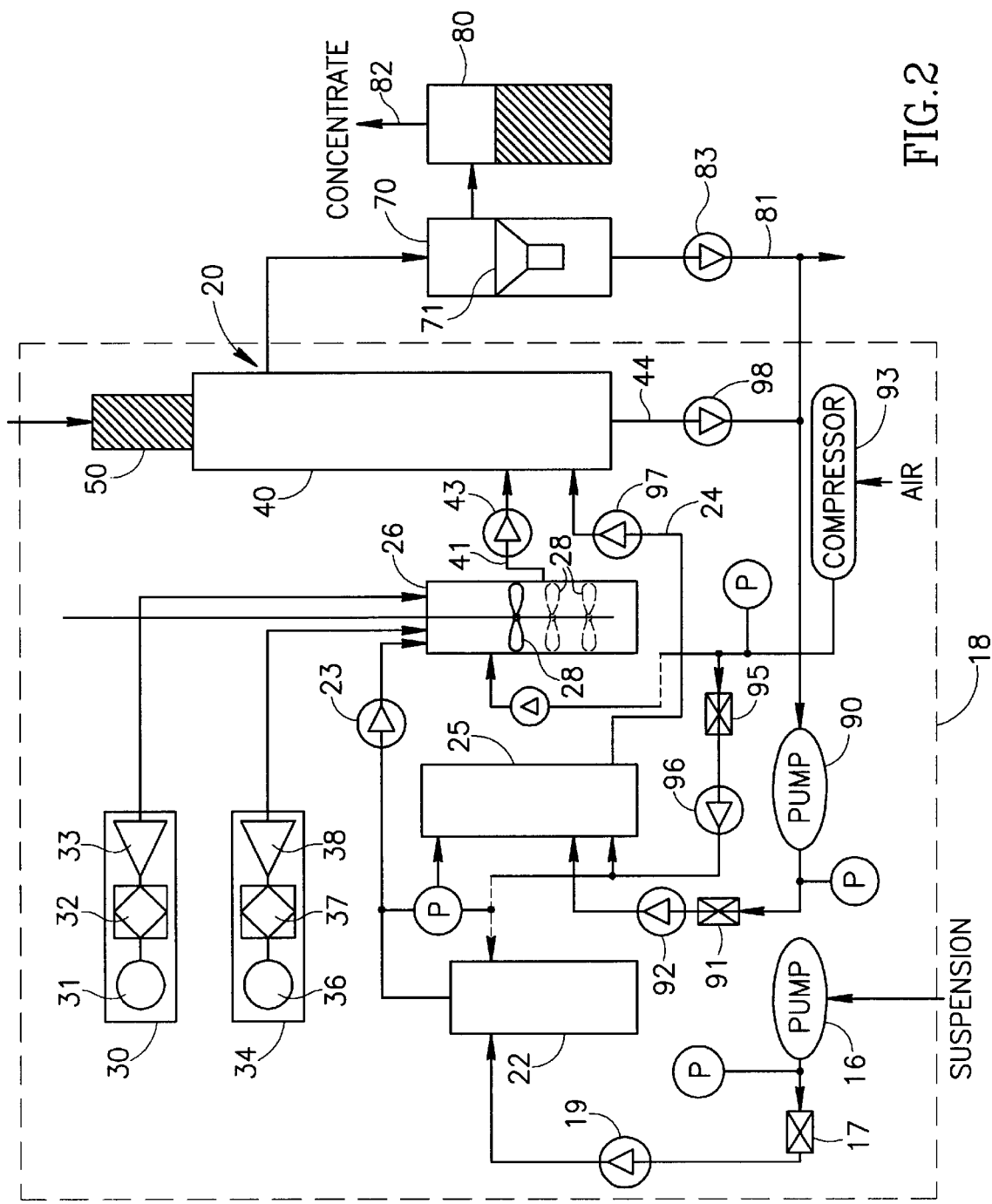
FIG. 2 schematically illustrates the process of separation of dry microalgae from suspension.

FIG. 2 shows a preferred embodiment of the microalgae separation process, constructed and operated in accordance with the principles of the present invention, showing further details of the microalgae separator 18 of FIG. 1.

Microalgae suspension from pond 12 is transferred by operation of pump 16 to reservoir 22. The rate of flow of the suspension is measured by a flowmeter 17 and can be regulated by a valve 19.

Pressure is monitored at various points of the system by pressure gauges P to facilitate smooth operation.

Suspension from reservoir 22 is passed to a mixer unit 26, which has a mixing device 28 of variable speed, where flocculation is carried out. Flow velocity is controlled by a valve 23. Flocculation involves treating of microalgae with a flocculant 30, added by means of a pump 31, measured by a dosimeter 32 and controlled by a valve 33, then bringing the microalgae into contact with each other by stirring with mixing device 28 so that aggregation can occur.

The pH of the suspension is first checked and brought to a value of less than 7 if necessary, by the addition of acid 34, which is added by operation of a pump 36. The amount of acid added is measured by a dosimeter 37 and is regulated by valve 38.

The concentration of the algae in suspension is checked by an optical density method in order to determine the amount of flocculant 30 required. Algae usually grow as a dilute suspension (200–500 mg/l). 100–300 g flocculate/ton of algae is used.

One of the flocculating agents used is modified starch, which is harmless in the subsequent use of algae. Other flocculating agents used include ferric chloride, aluminium sulphate and ketosones.

Flocculating agent 30 is added to the microalgae suspension in mixer unit 26. The mixture is then stirred by operation of mixing device 28 at a speed of 90 cycles/min for 5 minutes, after which time destabilization is essentially complete, then at 30 cycles/min for 15 minutes to bring particles into contact so that aggregates can form. The mixture is then left for flocculation to occur.

After the flocculation stage, the suspension is directed to flotation column 40 via inlet 41, regulated by valve 43.

Water and carbon dioxide (or air) are fed into a hydraulic saturator 25 at 6 atm to dissolve the gas in water. Water is fed in by pump 90, measured by flowmeter 91 and regulated by valve 92. CO2 is fed in from compressor 93, with flow rate measured by flowmeter 95 and regulated by valve 96.

The dissolved gas in water is transferred to flotation column 40 through a disperser 24, forming tiny bubbles. Flow rate of dissolved gas in water is controlled by valve 97. A layer of foam containing microalgae is formed on the liquid layer in the column, which can be skimmed off through the overflow outlet 20, the position of which is adjusted by piston 50. Purified water passes out of column 40 via outlet 44, controlled by valve 98.

After removal from flotation column 40 via overflow outlet 20, the foam containing microalgae is passed to a filtration unit 70, filtered through cloth in a filter 71, dried in a drying chamber 80 and packed, resulting in dry, biomass concentrate 82. Water is returned into the basic process via outlet 81, controlled by valve 83.

Figure 3:
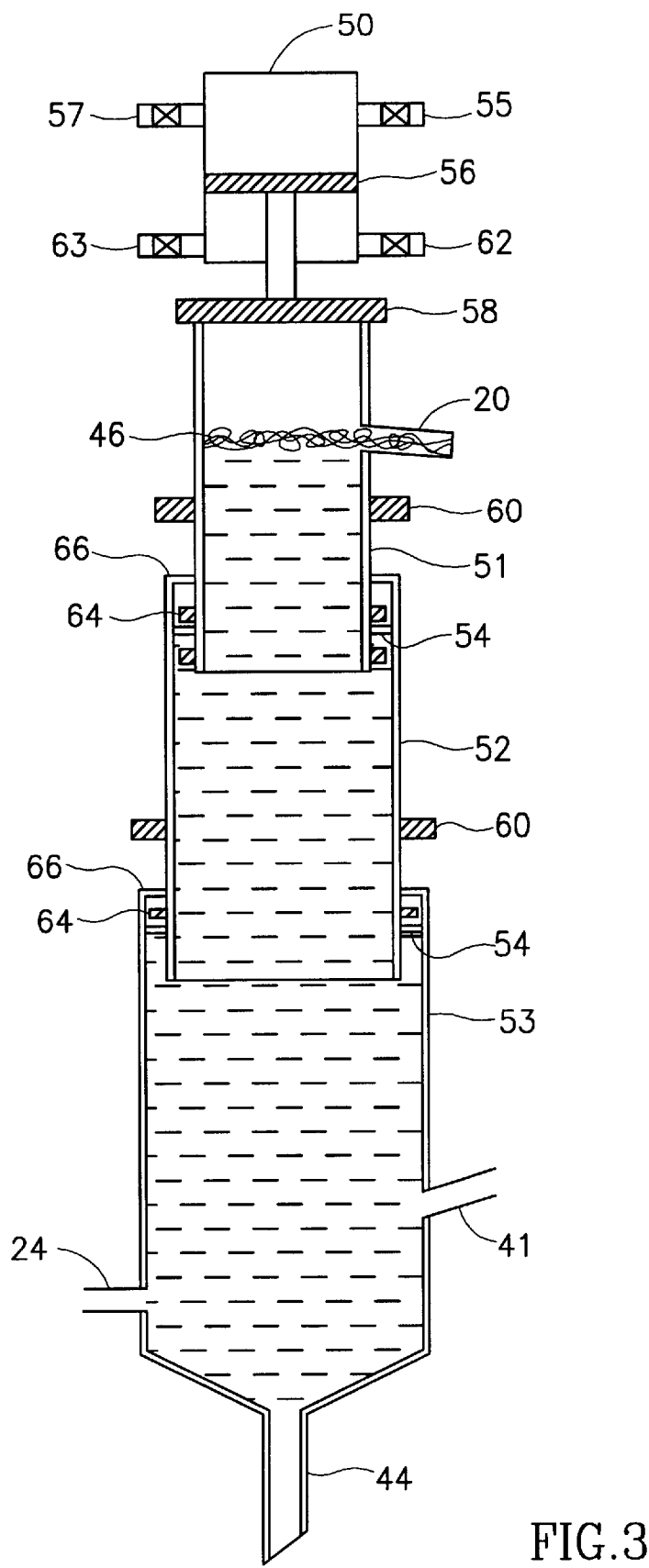
FIG. 3 illustrates the column flotation apparatus, according to the invention.

FIG. 3 shows the flotation column 40. Suspension containing flocculated microalgae is fed into column 40 via inlet 41. Dissolved gas in water is fed into flotation column 40 through disperser 24 under atmospheric conditions. The change in pressure permits the gas to come out of solution, which forms tiny bubbles. Disperser 24 consists of perforated rubber tubes, which ensure uniformity of the bubbles.

As the bubbles form, they collide with microalgae flocs, which become electrostatically adsorbed. The lower density of the gas relative to the medium causes bubble-microalgae agglomerates to float to the surface of the liquid and accumulate as a foam layer 46. The main factor governing flotation is the relative motion of flocs and bubbles, which determines the probability of bubble-particle attachment, bubble charging and flotation rate.

Column apparatus have the advantage of absence of rotating parts; low power requirements; large aerated volume; possibility of controlling air-flow rate and dispersion; small floor space and low capital investment.

The foam containing the algae is skimmed off at the top of the flotation column 40 through an overflow outlet 20. The purified water remaining in the column after removal of algae is discharged through an outlet 44 at the bottom of the column. The flotation process is regulated through the water and gas flow rates.

The flotation column 40 has a telescopic structure, enabling the position of overflow outlet 20 to be adjusted by contracting or expanding the height of the column 40. This is an improvement over conventional flotation columns in which the overflow outlet is fixed, so that the foam layer must be adjusted to the height of the outlet, and any part of the layer remaining below the level of the outlet remains in the column. The height of column 40 is adjusted by operation of a piston 50, so that the position of the overflow outlet 20 can be adjusted according to the position of the foam layer 46, allowing foam to easily overflow from the surface of the liquid. Adjustment of column height via the piston 50, may be carried out manually, or automatically by employing a sensor to detect the position of the foam layer, such as the float-type level transducer model NM produced commercially by KOBOLD Messring GmBH, Germany.

Column 40 consists of a series of concentric tubes 51, 52, 53 stacked one inside the other, held in position by rubber rings 54 situated between the outer wall of one tube and the inner wall of the tube of greater diameter in which the first tube is positioned. Frictional force between the rings 54 and the surface of the walls of the tube of greater diameter on one side and the surface of the walls of the tube of lesser diameter on the other side is able to retain the relative positions of the two tubes and thereby maintain the arrangement of the column in the required position i.e. in which the position of the overflow outlet corresponds to the foam layer in the column.

Alteration of the height of the column requires provision of a force of magnitude greater than the frictional force acting between the rubber ring and the walls of the two tubes between which the ring is situated. This may be provided by piston 50 or other means.

In accordance with the preferred embodiment of the present invention, piston 50 employing a high pressure air system is used. Air under high pressure enters the upper compartment of piston 50 through valve 55, thereby exerting a force on plunger 56, which causes it to be pushed down. High-pressure air leaves the upper compartment of piston 50 via valve 57. Push-rod 58 of plunger 56 has a rigid constraint with upper tube 51 of column 40, therefore forced downward movement of plunger 56, together with push-rod 58, causes simultaneous downward movement of column 40.

When the column height is altered, the ring 54 is in a fixed position relative to the outer surface of the tube of smaller diameter and moves relative to the inner surface of the tube of greater diameter. Piston 50 acts directly on the uppermost tube 51 of the column 40. Projection rings 60 are situated below the overflow outlet 20 on the outer surface of the uppermost tube 51. As the uppermost tube 51 is pushed downwards, these projection rings 60 make contact with the upper surface of the second tube 52, causing pressure to be exerted on the second tube 52. When this pressure exceeds the frictional force between the outer wall of the second tube 52 and the rubber rings 54 holding the tube 52 in position, the second tube 52 will be pushed downwards.

In order to raise the tubes 51, 52, 53 and increase the height of column 40 after the tubes have been lowered, high pressure air is fed into the lower compartment of piston 50 through valve 62, pushing plunger 56, together with push-rod 58 upwards. This causes tube 51 to be raised. High-pressure air leaves the lower compartment of piston 50 via valve 63.

Tubes 51 and 52 are provided with integrally formed projection rings 64 on their lower ends, which, when raised, engage with the upper rims 66 of the tubes of greater diameter (52 and 53 respectively). By this method, once tube 51 is raised to its maximum height, tube 52 will be engaged by projection rings 64 of tube 51, and continued upward pressure applied to plunger 56 will cause tube 52 to begin its upward motion.

Similarly, upon tube 52 reaching its maximum height, tube 53 will be engaged by projection rings 64 provided on tube 52. Tube 53 is supported by a stand (not shown) which prevents tube 53 from being pulled upwards. Therefore, once projection ring 64 of tube 52 engages with upper rim 66 of tube 53, column 40 has attained its maximum height.

Removal of solid biomass from aqueous suspension is carried out periodically in a filtration unit 70. After filtration, the biomass is further dehydrated in a drying chamber 80, resulting in dry, concentrated biomass 82.

In summary, the present invention provides a cheap, simple and efficient method of separating microalgae from water, requiring low energy consumption, which does not cause rupturing of the cell. The end result is dry, concentrated biomass in which cells remain intact, thereby retaining all important properties and constituents of the microalgae.

Having described the invention with regard to certain specific embodiments, it is to be understood that the description is not meant as a limitation since further modifications may now suggest themselves to those skilled in the art and it is intended to cover such modifications as fall within the scope of the appended claims.

We claim:

1. A method for the separation of dry biomass from an aqueous solution of microalgae, while maintaining the integrity of the cell structure, comprising the steps of:
   a) obtaining an aqueous suspension of the algae from a source thereof;
   b) adding a flocculating agent causing flocculation of the microalgae in suspension;
   c) introducing said flocculated suspension into a froth flotation column;
   d) dispersing a gas into fine bubbles for contact with said flocculated suspension;
   e) adsorbing said flocculated microalgae onto said bubbles to form bubble and algae agglomerates;
   f) forming, in an adaptable height column, a layer of froth containing said bubble and algae agglomerates;
   g) removing said froth containing bubble and algae agglomerates from said flotation column via an overflow outlet, by adjusting said column height; and
   h) further drying said froth.

2. The method of claim 1 wherein said froth forming step is performed in a flotation column comprising a telescopic column of adjustable height, said column comprising a series of concentric tubes of increasing diameter stacked one inside the other and held in selected positions by means of rubber rings situated between the outer wall of one tube and the inner wall of the tube of greater diameter in which the first tube is situated.

3. The method of claim 1 in which the step of removing said froth from said flotation column comprises adjusting the position of said overflow outlet to correspond to the position of said froth layer by adjusting the height of said telescopic flotation column.

4. The method of claim 1 wherein the height of said telescopic flotation column is adjusted by operating a piston or other mechanical means having a rigid constraint with the uppermost of said concentric tubes.

5. The method of claim 1 wherein subsequent tubes are lowered by projection rings integrally formed on sides of upper said concentric tubes which push down said subsequent tubes upon lowering of said upper tubes.

6. The method of claim 1 wherein said subsequent tubes are raised by engaging projection rings integrally provided on the sides of lower ends of each said upper tubes with the upper rim of each said subsequent tube.

7. The method of claim 1 wherein the step of further drying comprises drying in a drying chamber.

8. The method of claim 1 used in a system for production of microalgae as biofuel.

9. The method of claim 1 used in a system for production of microalgae as a health food.

10. The method of claim 1 used in a system for production of microalgae for pharmaceutical use.

11. The method of claim 1 used in a sewage treatment system.

12. An apparatus comprising:
   a) a reservoir containing an aqueous suspension of microalgae;
   b) a mixer unit into which said suspension of microalgae from said reservoir is introduced together with a flocculating agent for the purpose of providing mixing of said microalgae with said flocculating agent, causing flocculation of said microalgae;
   c) a froth flotation column into which said flocculated microalgae are introduced, said froth flotation column having an overflow outlet of adjustable height;
   d) means of dispersing a gas into fine bubbles for contact with said flocculated suspension in said flotation column in order to form a layer of froth containing agglomerates of bubbles and algae, such that when said froth layer is formed in said adjustable height froth flotation column, said overflow outlet removes said froth;
   e) means of mechanically filtering said froth; and
   f) an additional means of drying froth after filtration.

13. The apparatus of claim 12 wherein said froth flotation column comprises a telescopic column of adjustable height, consisting of a series of concentric tubes of increasing diameter stacked one inside the other and held in selected positions by means of rubber rings situated between the outer wall of one tube and the inner wall of the tube of greater diameter in which the first tube is situated.

14. The apparatus of claim 12 wherein said froth is removed from said flotation column via an overflow outlet by adjusting the position of said outlet to correspond to the position of said froth layer by adjusting the height of said telescopic flotation column.

15. The apparatus of claim 12 wherein height of said telescopic flotation column is adjusted by operating a piston or other mechanical means.

16. The apparatus of claim 15 wherein said piston is operated manually.

17. The apparatus of claim 15 wherein said piston is operated automatically in response to the position of said froth layer.

18. The apparatus of claim 12 wherein the means of drying said froth comprises a drying chamber.

* * * * *